United States Patent
Lequoy et al.

(10) Patent No.: US 11,247,077 B2
(45) Date of Patent: Feb. 15, 2022

(54) **SYNERGISTIC EXTRACT OF *PALMARIA PALMATA* AND JASMINE, COMPOSITIONS COMPRISING SAME AND USES THEREOF**

(71) Applicants: ISP INVESTMENTS LLC, Wilmington, DE (US); LVMH RECHERCHE, Saint-Jean de Braye (FR)

(72) Inventors: Valérie Lequoy, Valbonne (FR); Frédérique Portolan, Valbonne (FR); Audrey Le Mestr, Antibes (FR); Christophe Capallere, Nice (FR); Isabelle Imbert, Cannes (FR); Joël Mantelin, Cannes (FR); Jean Marie Botto, Valbonne (FR); Nouha Domloge, Opio (FR); Noëlle Garcia, Maganosc (FR); Carine Nizard, Vitry-sur-Seine (FR); Laurine Bergeron, Antibes (FR)

(73) Assignees: ISP INVESTMENTS LLC, Wilmington, DE (US); LVMH RECHERCHE, Saint-Jean de Braye (FR)

( * ) Notice: Subject to any disclaimer, the term of this patent is extended or adjusted under 35 U.S.C. 154(b) by 227 days.

(21) Appl. No.: 15/773,880

(22) PCT Filed: Nov. 4, 2016

(86) PCT No.: PCT/IB2016/056648
§ 371 (c)(1),
(2) Date: May 4, 2018

(87) PCT Pub. No.: WO2017/077497
PCT Pub. Date: May 11, 2017

(65) Prior Publication Data
US 2018/0344623 A1    Dec. 6, 2018

(30) Foreign Application Priority Data

Nov. 4, 2015   (FR) ..................................... 1560569

(51) Int. Cl.
*A61K 36/00*    (2006.01)
*A61K 36/63*    (2006.01)
*A61Q 19/08*    (2006.01)
*A61K 8/9728*   (2017.01)
*A61K 8/9717*   (2017.01)
*A61K 8/9789*   (2017.01)

(52) U.S. Cl.
CPC ............ *A61Q 19/08* (2013.01); *A61K 8/9717* (2017.08); *A61K 8/9728* (2017.08); *A61K 8/9789* (2017.08); *A61K 2800/805* (2013.01)

(58) Field of Classification Search
None
See application file for complete search history.

(56) References Cited

U.S. PATENT DOCUMENTS

2015/0238576 A1 * 8/2015 Richon .............. A61K 38/4873
424/94.65

FOREIGN PATENT DOCUMENTS

| CN | 103393557 A | * | 11/2013 |
| CN | 103550119 A | * | 2/2014 |
| FR | 2826575 A1 | | 1/2003 |
| FR | 2911278 A1 | * | 7/2004 |
| FR | 2999425 A1 | | 6/2014 |
| KR | 2007068949 A | * | 2/2007 |

OTHER PUBLICATIONS

International Search Report and Written Opinion issued in PCT/IB2016/056648 dated Jan. 16, 2017 (11 pages).

* cited by examiner

Primary Examiner — Michael Barker
Assistant Examiner — Randall O Winston
(74) Attorney, Agent, or Firm — Hamre, Schumann, Mueller & Larson, P.C.

(57) ABSTRACT

The present invention relates to a synergistic extract of *Palmaria palmata* and of jasmine flower heads, obtained after aqueous extraction of *Palmaria palmata*, in which maceration of the jasmine flower heads is then carried out, the ratio of the dry weight of *Palmaria palmata* to the dry weight of the flower heads being between 40/60 and 95/5. The present invention also relates to a method for obtaining said synergistic extract and cosmetic compositions comprising said extract as an active agent.
The invention finally relates to the cosmetic use of said composition for combating the signs of aging and for improving the elasticity of the skin, by favoring maintenance of the "stem" character of the adult dermal stem cells (SKPs).

8 Claims, 7 Drawing Sheets

SYNERGISTIC EXTRACT OF *PALMARIA PALMATA* AND JASMINE, COMPOSITIONS COMPRISING SAME AND USES THEREOF

FIELD OF THE INVENTION

The present invention relates to the field of cosmetics and notably to care of the skin by action at the level of the dermis. It relates more particularly to a synergistic extract of a plant of the genus *Jasminum* (also called jasmine) and of the red alga *Palmaria palmata*, a method of obtaining said extract, compositions comprising said extract and cosmetic uses thereof for combating the signs of aging of the skin, and notably for improving the elasticity, flexibility and firmness of the skin.

BACKGROUND OF THE INVENTION

Aging corresponds to the set of processes, notably physiological, that alter the structure and functions of the body over time. A distinction is made between two types of aging, namely intrinsic aging on the one hand, and extrinsic aging on the other hand. Intrinsic aging is due to genetic factors, to biochemical changes that take place during states of fatigue, stress, hormonal changes such as during pregnancy, etc. Extrinsic aging is, for its part, due to environmental factors to which the body is subjected throughout life, such as pollution, sunlight, diseases etc. It is a slow, progressive process that affects all the cells of the body by various means and is manifested in various ways. For example, at the level of the skin, the latter's appearance is altered by the various types of internal or external aggression and we then see the development of wrinkles and lines, hyper- or hypo-pigmentation spots, dryness or even dehydration of the skin, thinning of the epidermis, elastosis, imperfections, and age spots.

The skin is a covering organ mainly made up of three cellular layers: epidermis, dermis, and hypodermis. The epidermis, which constitutes the surface of the skin, is anchored to the dermis by a matrix of various proteins called the dermoepidermal junction.

The epidermis consists of several layers of cells called keratinocytes, which are regenerated by the stem cells of the epidermis located in the basal membrane of the epidermis.

The dermis is the supporting tissue of the skin and consists predominantly of fibroblasts, elastin fibers and collagen fibers (70% of the dermal fibers), enveloped in an interstitial extracellular matrix of proteoglycans. Collagen and elastin fibers are synthesized in the fibroblasts. The neo-synthesis of tropoelastin fibers, firstly in the form of proelastin, is a process that is linked to the activity of the fibroblasts, which secrete these fibers in the extracellular space. After maturation, elastin, associated with fibrillin, represents the major component of the elastic fibers that endow the dermis with its elastic properties. Moreover, the fibroblasts make it possible to regenerate the connective tissue and contribute to repair of the skin after a wound. The fibroblasts, which are involved in many functions at the level of the skin, are thus essential for keeping the skin healthy and in good condition.

The activities of renewal, or repair of the skin structures when damaged, for example by UV radiation or wounds, imply the existence of adult dermal stem cells (Skin Derived Precursors or SKPs), notably located in the tissues such as the prepuce and hair follicles (Toma et al., 2005, *Stem cells* 23:727-737). The SKP cells are the main progenitors of dermal cells, in that they ensure renewal of the fibroblasts. They are involved in particular in the repair of skin wounds.

The SKP cells possess characteristics typical of stem cells in general; they have considerable capacity for self-renewal and differentiation (Li et al., 2010, *J Cell Sci.* 123:853-60) and are defined as cells expressing a set of molecular markers such as:

Nestin+: intermediate-filament protein expressed by many cells during development and in particular the cells of the neural crest. Its expression is transient and does not persist into adulthood.

OCT4+ (octamer-binding transcription factor 4): multipotency marker involved in the self-renewal of undifferentiated embryonic stem cells.

SOX2+ (sex determining region Y-box 2): transcription factor essential for maintaining self-renewal of undifferentiated embryonic stem cells.

Research for identifying active agents capable of combating skin aging has led to the marketing of numerous active agents, of varying efficacy. However, there is still a need to identify new compounds capable of delaying the appearance or of combating the signs of skin aging more effectively. The problem more particularly intended to be solved by the invention is to identify novel active agents capable of combating the main signs of skin aging occurring at the level of the extracellular matrix, most of the constituent proteins of which are produced by the fibroblasts.

Algae are widely used in cosmetics applications. Their potential for preventing aging and for improving the appearance and protection of human skin is known. The use of extracts of algae may improve the nutrition of the skin and the hair, while maintaining a good level of hydration.

Certain species of micro-algae are marketed for skin care. For example, extracts of *Arthrospira* and of *Chlorella* are well known in antiaging creams, anti-irritant products and refreshing or regenerating care products.

Furthermore, the species of the genus of alga *Palmaria*, in particular the species *Palmaria palmata*, are known to be effective in skin care. The alga *Palmaria palmata* is also called Dulce or Dulse. This seaweed is rich in minerals, especially fluoride, phosphorus, potassium, in vitamins, in proteins and in polysaccharides (xylans). FR2826575 describes the cosmetic use of xylans extracted from *Palmaria palmata*, more particularly for increasing the hydration of the stratum corneum, but also regeneration of the skin and hair by synthesis of fibronectin and fibroblast proliferation.

An aqueous extract of jasmine flowers, especially of the species *Jasminum officinale*, is a known source of flavonoids with antioxidant properties. The essential oil of jasmine is used in aromatherapy (antioxidant) and in dermatology (antiseptic and anti-inflammatory properties).

However, none of the known uses of an extract of *Jasminum officinale*, on the one hand, and of an extract of *Palmaria palmata*, on the other hand, suggests that these two extracts have, independently of one another, or in combination with one another, properties i) of increasing gene and/or protein expression of collagen, and/or ii) of increasing the stem character of the dermal stem cells.

A trend in modern cosmetics is the development of active products of natural origin, having not only effects as anti-wrinkle or antiaging agents, but also combining several properties and thus providing a wider spectrum of improvement of the signs of aging.

Now, the inventors have demonstrated that a new extract obtained from *Palmaria palmata* and from *Jasminum officinale* is of considerable interest for skin care, in that it has a synergistic effect on the dermal stem cells. This extract in fact makes it possible to increase the reserve of dermal stem cells and improves their function, which makes it possible to preserve and even restore the structure of the connective tissue of the dermis. This extract makes it possible to improve the mechanical properties of the skin, in particular its elasticity, as has been demonstrated in a ballistometry test, and thus combat certain signs of skin aging.

Surprisingly, the inventors discovered that the synergistic extract of *Palmaria palmata* and of jasmine flower heads used according to the invention notably offers the following advantages:

it increases the amount of biochemical markers associated with the "stem" character of the dermal stem cells (SKPs) and in particular Nestin+, OCT4+, SOX2+ in the dermal cells;

it increases skin elasticity, skin flexibility and/or skin firmness, it increases renewal of the skin;

it increases synthesis of proteins of the dermal extracellular matrix, for example collagen, in particular collagen I, III or V; procollagen, in particular procollagen I, III or V; and tropoelastin;

it consequently makes it possible to combat the cutaneous signs associated with skin aging.

"Stem character of the dermal stem cells" means the expression profile of biochemical markers associated with the phenotype of the SKP or SKP-like cells, in particular Nestin+, OCT4+, SOX2+ expression.

The invention and the advantages resulting therefrom will be better understood on reading the description.

DESCRIPTION OF THE INVENTION

Figure 1:
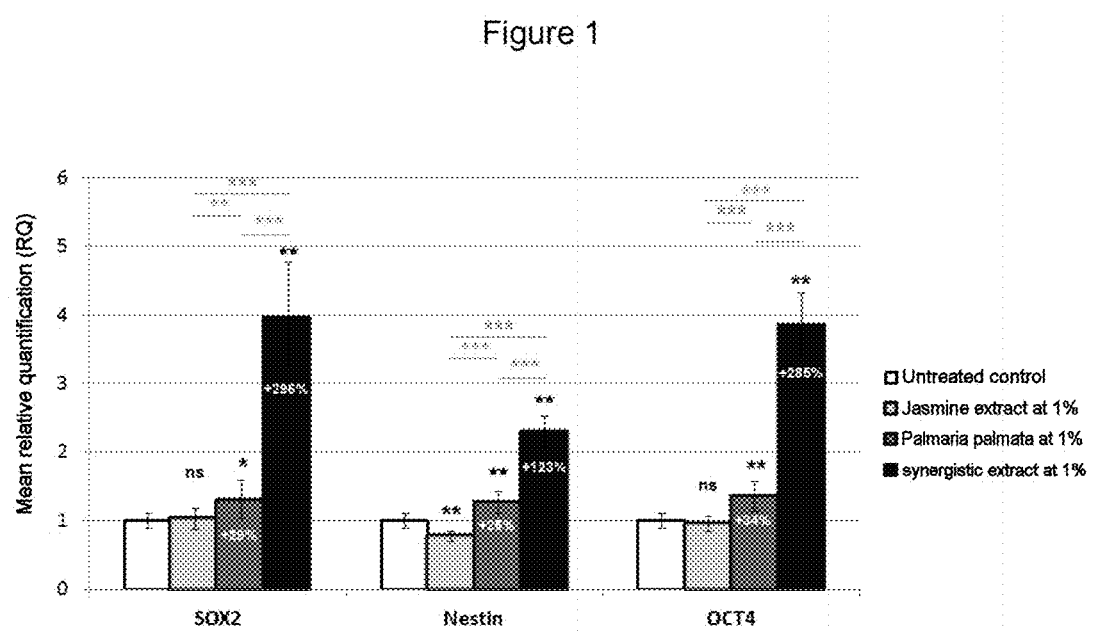
FIG. 1 is a chart showing expression of mRNAs of SOX2, Nestin and OCT4 from Example 2.

The present invention relates to an extract of a plant of the genus *Jasminum* obtained by maceration of at least part of the plant in an aqueous hydrolyzate of the alga *Palmaria palmata*. The weight ratio of the dry weight of the alga to the dry weight of the plant, both used as raw material for preparing the extract, is preferably between 40/60 and 95/5. This extract has the original feature that it does not have biological properties identical to those that are obtained with a mixture of an aqueous hydrolyzate of the alga *Palmaria palmata*, and of an extract of a plant of the genus *Jasminum* obtained by maceration of at least part of the plant in water.

The present invention relates firstly to a synergistic extract of the alga *Palmaria palmata* and of at least part of a plant of the genus *Jasminum*, said extract being obtainable by a method comprising i) a step of preparing an aqueous extract of the alga *Palmaria palmata* followed by ii) a step of maceration of at least part of a plant of the genus *Jasminum* in said aqueous extract, the weight ratio of the dry weight of the alga to the dry weight of the plant part, both used as raw material for preparing the synergistic extract, being between 40/60 and 95/5.

In one embodiment, the synergistic extract is obtained by this method.

In the present invention, percentages are expressed in weight/weight, unless stated otherwise.

In the rest of the description, the terms "jasmine" and "plant of the genus *Jasminum*" are used indiscriminately.

The term "extract" generally denotes an isolated substance, obtained from a native plant raw material, not previously existing as such in nature.

In the present description, mention of alga or plant means the harvested plant material, optionally dried (by any known method, such as stove drying or lyophilization), and optionally reduced to powder or flakes by grinding.

"Synergistic extract" according to the invention means an extract comprising or consisting of an aqueous extract of *Palmaria palmata* and of jasmine, preferably of flower heads of *Jasminum officinale*, capable of increasing the expression of Nestin+, OCT4+, SOX2+, either by increasing protein synthesis by direct or indirect modulation of gene expression, or by other biological processes such as stabilization of the protein or else stabilization of the messenger RNA transcripts, relative to a reference extract of *Palmaria palmata* incubated alone, a reference extract of jasmine incubated alone, and a mixture thereof. A reference extract of *Palmaria palmata* may be obtained for example by carrying out step i) of the method for preparing the synergistic extract as described above, in identical preparation conditions. A reference extract of jasmine may be obtained for example by carrying out step ii) of the method for preparing the synergistic extract as described above, in identical preparation conditions, by replacing the weight of aqueous extract of *Palmaria* obtained at the end of step i) with the same weight of water. Throughout the description, the increase in properties is evaluated at constant weight of dry matter of extract.

In particular, a synergistic extract according to the invention is an extract comprising or consisting of an aqueous extract of *Palmaria palmata* and of jasmine flower heads capable of multiplying, by at least 2, the stem character of dermal stem cells, relative to a reference extract of *Palmaria palmata* incubated alone, a reference extract of jasmine incubated alone, and optionally a mixture thereof.

In particular, the synergistic extract may be capable of:
multiplying, by at least 8, the amount of messenger RNA of SOX2+ expressed by fibroblasts, and/or
multiplying, by at least 2, the amount of messenger RNA of Nestin+ expressed by fibroblasts, and/or
multiplying, by at least 6, the amount of messenger RNA of OCT4+ expressed by fibroblasts,
relative to a reference extract of *Palmaria palmata* incubated alone, and a reference extract of jasmine incubated alone.

The terms "synergistic extract", "synergistic extract of *Palmaria palmata* and of jasmine flower heads" or "active agent" will be used as alternatives with the same meaning throughout the description.

The part of the plant of the genus *Jasminum* may be the root, stem, leaves, flowers or seeds. Preferably said part comprises the flowers. "Flower heads" means a part of the plant comprising the flower optionally accompanied by stem. In one embodiment, the flower heads comprise the flower and a few centimeters of stem.

The extract according to the invention is preferably obtained after aqueous extraction of *Palmaria palmata*, in which maceration of the jasmine flower heads is then carried out, the weight ratio of the dry weight of the alga to the dry weight of the flower heads being from 50/50 to 90/10, for example from 60/40 to 70/30 or from 80/20 to 90/10 (inclusive). In one embodiment, the weight ratio is equal to 90/10.

Preparation of the extract may begin with the preparation of an aqueous extract of *Palmaria palmata*, which is a species of red algae of the Palmariaceae family, also called Dulce or Dulse. It has been an important source of fibers for centuries. This alga is rich in minerals, in particular fluoride, phosphorus, potassium, minerals, vitamins, proteins and polysaccharides (xylans).

The aqueous extract of *Palmaria palmata* used according to the invention may be obtained by enzymatic hydrolysis, for example with a carbohydrase and/or an endoprotease, of an aqueous solution of *Palmaria palmata* comprising a weight ratio of water to *Palmaria palmata* (expressed in dry weight of the alga) between 10/1 and 50/1, at a pH between 3 and 6, at a temperature between 40 and 80° C., for a time of at least 1 hour, preferably 2 hours.

The algae of *Palmaria palmata* are advantageously dried and finely ground, after harvesting.

The weight ratio of water to *Palmaria palmata* is preferably between 15/1 and 30/1, even more preferably between 20/1 and 25/1.

The pH is preferably adjusted, for example by adding hydrochloric acid (HCl), between 3 and 6, preferably between 4 and 5.5, even more preferably between 4 and 4.5.

The hydrolysis temperature is preferably between 40° C. and 80° C., preferably between 50 and 60° C. and even more preferably it is 55° C.

The use of hydrolyzed plant extracts offers many advantages in cosmetics and dermocosmetics. Besides releasing active compounds, hydrolysis and purification make it possible to obtain mixtures that are more stable, more easily standardized, and that do not cause allergic reactions in cosmetics.

Advantageously, controlled hydrolysis allows access to the sugars contained in the algae of the species *Palmaria palmata*. The extract according to the invention is an aqueous extract of jasmine and *Palmaria* enriched with compounds of interest from *Palmaria palmata* and jasmine.

Controlled enzymatic hydrolysis is preferably carried out with a xylanase, as carbohydrase, and a bromelain, as endoprotease. These enzymes make it possible to optimize the yield and degree of hydrolysis.

The xylanases are enzymes of the glycosyl hydrolase group that catalyze the hydrolysis of β-1,4-glucosidics to xylan via a double displacement mechanism. Hydrolysis of xylans releases xylose.

Preferably, the endoprotease used in the method according to the invention is bromelain, also called bromelase. It is a proteolytic enzyme extracted from the fresh stems and roots of the pineapple. It is a mixture of enzymes with proteolytic action, which target the sulfated groups of the side chains of the cysteines.

Xylanase is used in an amount preferably between 2 and 6%, even more preferably 4% relative to the amount in dry weight of alga added to the reaction mixture and bromelain in an amount preferably between 1 and 3%, even more preferably 2%.

The aqueous extract of *Palmaria palmata* thus obtained is then separated from the solid residues by a method known by a person skilled in the art such as centrifugation followed by filtration.

It is this first filtered aqueous extract that will serve as maceration liquid for the jasmine flower heads, for example.

Maceration is a process that consists of leaving a solid in a liquid for a defined time, to extract the soluble compounds from it.

Preferably, maceration is carried out for a time of at least 2 hours and up to 4 hours at ambient temperature, for example at a temperature between 18 and 35° C.

*Jasminum officinale* or white jasmine (or common jasmine) is a climbing shrub, of the Oleaceae family, with deciduous to semi-persistent foliage, giving abundant perfumed blossom throughout the summer.

Jasmine flower heads (which comprise the flower, as plant part, and are accompanied by a few centimeters of stem) are preferably selected from the flower heads of one of the species *Jasminum grandiflorum, Jasminum officinale, Jasminum odoratissimum, Jasminum sambac, Jasminum auriculatum, Jasminum flexile*, preferably *Jasminum officinale*. The jasmine preferably belongs to the species *Jasminum officinale*.

The jasmine flower heads are advantageously used whole and dried and left to macerate in the aqueous extract of *Palmaria palmata*.

The synergistic extract of *Palmaria palmata* and of jasmine flower heads thus obtained, after filtration, has a dry matter content between 26.8 and 30.8 g/kg, a concentration of proteins between 1.3 and 2.3 g/kg and a concentration of sugars (mostly xylose) between 25.3 and 29.3 g/kg.

The extract may then be diluted in one or more physiologically acceptable solvents such as water, glycerol, ethanol, propanediol, butylene glycol, dipropylene glycol, ethoxylated or propoxylated diglycols, cyclic polyols or any mixture of these solvents. Preferably, the extract is diluted in water and xylitol to give a final extract at 30 wt % of xylitol. The synergistic extract according to the invention is then characterized by a concentration of dry matter between 280 and 320 g/kg, a concentration of sugars between 8 and 12 g/kg, and a pH between 4 and 5.

The invention relates secondly to a method of obtaining a synergistic extract of *Palmaria palmata* and of jasmine flower heads, comprising the following steps, according to which:

an amount of *Palmaria palmata* is dissolved in water in a weight ratio of water to *Palmaria palmata* (in dry weight) between 10/1 and 50/1;

the aqueous solution of *Palmaria palmata* is hydrolyzed with a carbohydrase and an endoprotease, at a temperature between 40 and 80° C.;

jasmine flower heads are macerated in the aqueous extract of *Palmaria palmata* obtained previously; the weight ratio of the dry weight of the alga to the dry weight of the flower heads being between 40/60 and 95/5.

the macerated product obtained is filtered and then heated for 2 to 24 hours, at a temperature between 40 and 90° C., to deactivate the carbohydrase and endoprotease enzymes.

According to a particular embodiment, the method for obtaining a synergistic extract of *Palmaria palmata* and of jasmine flower heads according to the invention comprises the following steps, according to which:

a) an amount of *Palmaria palmata* dried and finely ground in the form of flakes is dissolved in water in a weight ratio of water to *Palmaria palmata* between 10/1 and 50/1, preferably between 20/1 and 40/1.

b) the aqueous solution of *Palmaria palmata* is hydrolyzed with a carbohydrase and an endoprotease, preferably performed with a xylanase and a bromelain, at a pH between 3 and 6, preferably between 4 and 5.5, even more preferably between 4 and 4.5, at a temperature between 40 and 80° C., preferably between 50 and 60° C., even more preferably 55° C., for a time of at least 1 hour, preferably 2 hours;

c) after optional addition of a filter aid and centrifugation, an aqueous extract of *Palmaria palmata* is obtained;

d) dried jasmine flower heads are macerated for a time of at least 2 hours and at most 4 hours at ambient temperature in the aqueous extract of *Palmaria palmata* obtained in step c); the weight ratio of the dry weight of the alga to the dry weight of the flower heads being between 40/60 and 95/5. Preferably, the weight ratio of the dry weight of the alga to the dry weight of the flower heads is equal to 90/10;

e) the macerated product thus obtained in step d) is filtered to recover an extract of *Palmaria palmata* and of jasmine flower heads, which is heated for at least 2 hours and for up to 24 hours and preferably for 12 hours or overnight, at a temperature between 40 and 90° C., preferably at 80° C. to deactivate the carbohydrase and endoprotease enzymes; and f) it is purified optionally by filtration to obtain the synergistic extract of *Palmaria palmata* and of jasmine flower heads.

During step d), the jasmine flower heads are not necessarily macerated in a medium containing a glycol or more generally an alcohol such as methanol; the use of a liquid medium based on water only is preferred. Moreover, the step of maceration of the flowers in the aqueous extract of *Palmaria* does not necessarily comprise a step of enzymatic hydrolysis, which is sometimes envisaged in the prior art for extracting the phenolic compounds and carbohydrates from the flowers. Enzymatic hydrolysis is performed on the aqueous extract of *Palmaria*, before adding the jasmine flowers.

After steps b) and e), the solution obtained may be turbid. Steps of centrifugation and filtration are carried out to remove the suspended solid residues. A filter aid such as Celatom® may be added to the mixture, then a filtration step is carried out to separate the solids from the liquid phase, the solids being discarded. Several successive filtration steps on filters of decreasing porosity may then be performed. The filtrate collected constitutes the extract of *Palmaria palmata* rich in polysaccharides.

The filtrate resulting from enzymatic hydrolysis of *Palmaria palmata* and maceration of jasmine flower heads in the extract of *Palmaria*, after deactivation of the residual enzymes, constitutes a first form of the active synergistic extract according to the invention, or first filtrate. At this stage, the first filtrate has for example a concentration of dry matter between 26.8 and 30.8 g/kg, a content of protein compounds between 1.3 and 2.3 g/kg and a sugar content between 25.3 and 29.3 g/kg.

This first active filtrate may then be diluted in one or more physiologically acceptable solvents, such as water, glycerol, ethanol, propanediol, butylene glycol, dipropylene glycol, ethoxylated or propoxylated diglycols, cyclic polyols or any mixture of these solvents. In a preferred embodiment, the first active filtrate is diluted in a solvent mixture such that a second filtrate or final extract is obtained containing 30% of xylitol. The synergistic extract according to the invention may also be preserved from contaminants with 0.5% sodium benzoate.

The second filtrate diluted in a solvent may then be filtered under sterile conditions, pasteurized at low temperature, preferably at 65° C. overnight, for complete sterilization.

According to this embodiment, a final filtrate is obtained, which constitutes the synergistic extract according to the invention. The synergistic extract obtained according to the invention may be analyzed qualitatively and quantitatively, by the conventional techniques that are familiar to a person skilled in the art, to determine its physicochemical characteristics and its content of compounds.

Preferably, when the first active filtrate contains 30% of xylitol, the synergistic extract according to the invention is characterized by a concentration of dry matter between 280 and 320 g/kg, a concentration of sugars between 8 and 12 g/kg, and a pH between 4 and 5.

The present invention relates thirdly to a composition comprising, in a physiologically acceptable medium, for combating the signs of skin aging, the synergistic extract according to the invention at a concentration between 0.0001% and 20% dry weight of the total weight of the composition, and preferably at a concentration between 0.05% and 5% dry weight of the total weight of the composition.

"Physiologically acceptable" means that the synergistic extract according to the invention, or a composition containing said agent, is suitable for coming into contact with the skin or a mucous membrane, without causing a reaction of toxicity or intolerance.

The synergistic extract according to the invention may be encapsulated or included in a cosmetic or pharmaceutical carrier such as liposomes or any other microcapsule used in the field of cosmetics or adsorbed on organic polymers in powder form, or mineral supports such as talcs and bentonites.

These compositions may notably be in the form of an aqueous, aqueous-alcoholic or oily solution; an oil-in-water emulsion, water-in-oil emulsion or multiple emulsions; they may also be in the form of creams, suspensions, or powders, suitable for application on the skin, the mucosae, the lips and/or the appendages. These compositions may be more or less fluid and have the appearance of a cream, a lotion, a milk, a serum, an ointment, a gel, a paste or a foam. They may also be in solid form, such as a stick, or may be applied on the skin in the form of aerosol. They may be used as a skin care product and/or as a skin makeup product.

These compositions further comprise any additive commonly used in the field of application envisaged as well as the aids required for their formulation, such as solvents, co-solvents (ethanol, glycerol, benzyl alcohol), thickeners, diluents, antioxidants, dyes, sun filters, self-tanning agents, pigments, fillers, preservatives, perfumes, odor absorbers, cosmetic or pharmaceutical active ingredients, essential oils, vitamins, essential fatty acids, surfactants, trace elements, film-forming polymers, chemical or mineral filters, hydrating agents or hot spring water, polymers such as polysaccharides or polypeptides, cellulose derivatives of the methylcellulose type or hydroxypropylcellulose, or else synthetic polymers, poloxamers, carbomers, siloxanes, PVA or PVP.

In all cases, a person skilled in the art will take care that these additives as well as their proportions are selected in such a way that they do not adversely affect the required advantageous properties of the composition according to the invention. These additives may, for example, correspond to 0.01 to 20% of the total weight of the composition. When the composition of the invention is an emulsion, the oily phase may represent from 5 to 80 wt % and preferably from 5 to 50 wt % relative to the total weight of the composition. The emulsifiers and co-emulsifiers used in the composition will be selected from those used conventionally in the field in question. For example, they may be used in a proportion from 0.3 to 30 wt %, relative to the total weight of the composition.

The composition usable according to the invention may be applied by any suitable route, notably oral or external topical, and the formulation of the compositions will be adapted by a person skilled in the art.

Advantageously, the compositions according to the invention are in a form suitable for topical application. These compositions must therefore contain a physiologically acceptable medium, i.e. which is compatible with the skin and the appendages, and includes all cosmetic forms.

Advantageously, the composition usable for implementing the invention may comprise, besides the active agent according to the invention, at least one other active agent having cosmetic effects similar and/or complementary to those of the invention. According to the invention, this active agent will be defined as an "additional active agent".

For example, the additional active agent or active agents may be selected from: antiaging agents, firming agents, lightening agents, hydrating agents, draining agents, favoring the microcirculation, pharmaceutical agents, exfoliating agents, desquamating agents that stimulate the extracellular matrix, activating energy metabolism, antibacterials, antifungals, soothing agents, anti-free-radical agents, anti-UV agents, anti-acne agents, anti-inflammatories, anesthetic agents, providing a sensation of heat, providing a sensation of freshness, and slimming agents.

These additional agents may be selected from the groups comprising:
- vitamin A and notably retinoic acid, retinol, retinol propionate, retinol palmitate,
- vitamin B3 and more particularly nicotinamide, tocopherol nicotinate,
- vitamin B5, vitamin B6, vitamin B12, panthenol,
- vitamin C, notably ascorbic acid, ascorbyl glucoside, ascorbyl tetrapalmitate, magnesium and sodium ascorbyl phosphate,
- vitamins E, F, H, K, PP, coenzyme Q10,
- metalloproteinase inhibitors, or a TIMP activator,
- DHEA, precursors and derivatives thereof,
- amino acids such as arginine, ornithine, hydroxyproline, hydroxyproline dipalmitate, palmitoylglycine, hydroxylysine, methionine and derivatives thereof, N-acyl amino acid compounds,
- natural or synthetic peptides, including the di-, tri-, tetra-, penta- and hexapeptides and their lipophilic derivatives, isomers and complexes with other species such as a metal ion (e.g. copper, zinc, manganese, magnesium, and others). For example, the peptides known commercially by the name MATRIXYL®, ARGIRELINE®, COLLAXYL™, PEPTIDE VINCI 02™, CHRONOGEN™, LAMINIXYL IS™, PEPTIDE Q10™, the synthetic peptide of sequence Arg-Gly-Ser-NH$_2$, marketed under the name ATPeptide™, the synthetic peptide of sequence Pro-Leu-Asp-Thr-Ala-Lys-Val-Arg-Leu-Gln marketed under the name SIRPeptide™.
- plant peptide extracts such as extracts of soybean, spelt, grapevine, colza, flax, rice, maize, or pea,
- yeast extracts, extracts of *Artemia salina*,
- dehydroacetic acid (DHA),
- phytosterols of synthetic or natural origin,
- salicylic acid and derivatives thereof, alpha- and beta-hydroxy acids, silanols,
- amino sugars, glucosamine, D-glucosamine, N-acetyl-glucosamine, N-acetyl-D-glucosamine, mannosamine, N-acetyl mannosamine, galactosamine, N-acetyl galactosamine,
- extracts of polyphenols, isoflavones, flavonoids, such as grape extracts, pine extracts, olive extracts,
- lipids such as ceramides or phospholipids, oils of animal origin, such as squalene or squalane; vegetable oils, such as sweet almond oil, copra oil, castor oil, jojoba oil, olive oil, colza oil, groundnut oil, sunflower oil, wheat germ oil, maize germ oil, soybean oil, cotton oil, alfalfa oil, poppy oil, pumpkin oil, evening primrose oil, millet oil, barley oil, rye oil, safflower oil, passionflower oil, hazelnut oil, palm oil, apricot kernel oil, avocado oil, calendula oil; ethoxylated vegetable oils, shea butter,
- UV screens and sun filters.

Another aspect of the invention relates to the cosmetic use of a synergistic extract of *Palmaria palmata* and of jasmine flower heads according to the invention, for combating the signs of aging of the skin, notably by favoring maintenance of the "stem" character of the SKP adult dermal stem cells.

The invention relates to mammals and to human beings in particular.

"Signs of skin aging" means any changes in the external appearance of the skin and appendages due to intrinsic and extrinsic aging, for example wrinkles and lines, withered appearance, loss of firmness, thinning, loss of elasticity and/or of tone, dullness and loss of radiance, but also any internal change of the skin that is not always reflected in an altered external appearance, for example any internal degradation of the skin caused by external factors such as ultraviolet radiation (UV). The active agent according to the invention, or the composition containing it, will make it possible in particular to combat loss of elasticity, flexibility and firmness of the skin.

"Combating the signs of skin aging" means delaying the appearance, reducing, improving the visual appearance, or else correcting such signs. In particular, "combating the signs of aging" means improving the mechanical properties of the skin, notably increasing its firmness, flexibility and/or elasticity.

Thus, the invention further relates to the cosmetic use of a synergistic extract of *Palmaria palmata* and of jasmine flower heads for improving the elasticity of the skin.

The invention further relates to the cosmetic use of a synergistic extract of *Palmaria palmata* and of jasmine flower heads for improving the elastic properties of the skin.

The term "skin" according to the invention includes the hairless skin and all the keratinous appendages present on the surface of the body, in particular bristles, eyelashes, eyebrows, nails and the hair.

The permanent renewal of the skin, but also repair thereof after damage such as by UV radiation or wounds, implies the existence of somatic stem cells called dermal stem cells or SKPs in the skin. This reserve of stem cells decreases during aging and under the aggressive action of external factors, lessening the capacity for renewal of the skin and contributing to the appearance of signs of aging of the skin.

The expression "external aggressive factor" means the aggressive factors in the environment. As an example, we may mention factors such as pollution, ultraviolet radiation, or products of an irritant nature such as surfactants, preservatives or perfumes. Pollution means both "external" pollution due for example to diesel particles, ozone or heavy metals, and "internal" pollution, which may notably be due to emissions from paint solvents, glues, or wallpaper (such as toluene, styrene, xylene or benzaldehyde), or cigarette smoke. Dryness of the atmosphere is also an important cause of dry skin.

Now, the inventors found that, surprisingly, the active agent according to the invention protects the SKP cells and reinforces their activity. In fact, the extract according to the invention allows a synergistic increase of the markers that are characteristic of the "stem" character of the dermal stem cells, much greater than the activation observed after treatment with an extract of *Palmaria palmata* alone or with an aqueous extract of jasmine flower heads alone.

The synergistic extract may thus be used an as active agent in a cosmetic composition for preventing or repairing the skin damage caused by aging, possibly accelerated by exposure to the sun or to a drying environment.

Thus, one aspect of the invention relates to the cosmetic use of an extract of jasmine flower heads obtained by maceration of said heads in an aqueous extract of *Palmaria palmata*, for improving at least one of the conditions of an area of healthy skin of a person, selected from the group consisting of skin firmness, skin elasticity, skin flexibility and the skin renewal rate.

In the sense of the present invention, "cosmetic use" means a use that is not intended for therapeutic use. In the context of this use, the extract is applied on a part of a person's skin that is healthy. An area of healthy skin can easily be characterized by a dermatologist, who does not detect any disease, any skin disorder (psoriasis, eczema or acne) or any wound.

During aging, there is an overall decrease in the amount of collagen, which leads to a loss of skin firmness. This phenomenon may be accelerated when the skin is subjected to external aggressive factors such as cold or UV radiation.

Skin aging is manifested by various signs, which have biological causes independent of one another, so that it is possible to combat aging of the skin by proposing active ingredients that act upon particular targets to induce a decrease in a particular sign of aging.

These manifestations include loss of firmness, increase in stiffness and loss of elasticity. Degradation of the mechanical properties of the skin is mainly due to the decrease in the amount of collagen in the dermal extracellular matrix. This decrease is itself due to various causes that are independent of one another, including degradation of the collagen molecules by enzymes, glycation of these same molecules, and decrease in the production of collagen by the fibroblasts.

Biological active ingredients with an antiaging effect known by a person skilled in the art that are incorporated in cosmetics compositions inhibit the activity of the collagenases, which are responsible for the degradation of collagen. Other active ingredients that inhibit the collagen glycation mechanism have also been proposed in cosmetic care products. These active ingredients and these cosmetic compositions slow the degradation and the breakdown of collagen fibers. Such products do not make it possible to increase the amount of newly synthesized dermal proteins, or the cellular renewal rate.

Therefore there is still need to propose biological active ingredients that are more effective for combating the signs of skin aging. The aim of the present invention is to provide a new extract of plant origin that makes it possible not only to stabilize the amount of collagen in the skin over time, but increase the gene and/or protein expression of collagen, and consequently improve the mechanical properties of the skin, such as flexibility and elasticity.

According to one of its aspects, the invention relates to the use of the extract described above or prepared by the method described above for combating aging of the skin, by increasing its level of flexibility, its level of elasticity, and/or its cellular renewal rate.

The increase in skin flexibility and elasticity produced by the extract of the invention may be linked to the increase in expression of at least one protein of the extracellular matrix of the dermis selected from collagen, tropoelastin and procollagen. The increase in expression of a protein in the dermis may correspond to an increase in gene expression and/or protein expression of said protein. In a particular embodiment, the increase in skin firmness and elasticity is caused by simultaneous increases in the synthesis of collagen and of elastin, for example by simultaneous increase in the syntheses of collagen I, collagen III, procollagen I, procollagen III, and tropoelastin.

Increase in cellular renewal of the skin may be reflected in the increase in the number of dermal stem cells and/or in the improvement of their functioning, which makes it possible to restore the structure of the dermal connective tissue that had deteriorated before application of the synergistic extract. In a particular case, the invention aims to restore or enhance the stem character of the dermal stem cells by increasing expression of at least one of the markers Nestin+, OCT4+ and SOX2+ expressed by fibroblasts.

The invention relates more particularly to the cosmetic use of an extract of jasmine flower heads obtained by maceration of said heads in an aqueous extract of *Palmaria palmata*, for combating aging of the skin by increasing the firmness, flexibility and/or elasticity of the skin. The increase in firmness, flexibility and/or elasticity may be induced by increasing the synthesis of proteins by the fibroblasts in the dermis.

The invention also relates to the cosmetic use of an extract of jasmine flower heads obtained by maceration of said heads in an aqueous extract of *Palmaria palmata*, for increasing cellular renewal of the dermis notably by increasing the stem character of the dermal stem cells (SKPs) and/or by increasing the quantity of dermal stem cells in the skin.

The present invention also relates to the cosmetic use, advantageously by the topical route, of the extract described above, for increasing the expression of at least one protein of the dermis. The increase in expression of a protein in the dermis may correspond to an increase in gene expression and/or protein expression of said protein. This protein is for example selected from collagen, tropoelastin and procollagen. The collagen is preferably collagen I or collagen III. The procollagen is preferably procollagen I, or procollagen III. In a particular embodiment, the invention relates to the use of the extract for simultaneously increasing protein expression of procollagen I, protein expression of collagen III, and protein expression of tropoelastin.

The increase in expression of the collagen of the dermis may be an increase in the protein expression level of collagen of at least 15% relative to the protein expression level of collagen measured in the absence of the extract according to the invention. This increase is preferably measured in dermis equivalents containing fibroblasts and dermal stem cells of the SKP or SKP-like type obtained from adult donor fibroblasts, using an amount of dry extract by weight of the order of 0.01% of the weight of the dermis equivalent. For example, it is an increase in the protein expression level of procollagen I and collagen III of at least 20% in dermis equivalents, measured for example according to the protocol as described in example 3, using an immunolabeling method with detection by observation with an epifluorescence microscope, optionally combined with an increase in the protein expression level of tropoelastin of at least 15% in dermis equivalents, measured for example according to the protocol as described in example 5, using an immunolabeling method with detection by observation with an epifluorescence microscope.

The increase in flexibility and/or elasticity may be an increase of at least 15% relative to the level of flexibility or of elasticity respectively, of a sample of skin measured before application of the extract according to the invention. The increase in flexibility and elasticity may be measured using a ballistometer on dermis equivalents containing fibroblasts and dermal stem cells of the SKP or SKP-like type, using an amount of extract equivalent to a dry weight of the order of 0.01 wt % of the weight of culture medium.

The method of ballistometry consists of tracking the oscillations of a ball that is dropped onto a sample of skin from a predetermined height. The depth of penetration of the ball when released (called indentation) makes it possible to measure the rigidity, and consequently the flexibility of the skin. In fact, the deeper the penetration of the ball, the lower is the rigidity of the skin. The elasticity is evaluated by calculating the slope of the curve (called alpha) joining all the tops of the oscillation peaks. The more elastic the skin, the more the ball bounces, and the lower the slope. The increase in flexibility, which may also be expressed as the decrease in rigidity, is for example a decrease in indentation of at least 15% relative to the indentation measured before application of the extract according to the invention, using a method of ballistometry on dermis equivalents containing fibroblasts and dermal stem cells of the SKP or SKP-like type, in particular according to the protocol of example 6.

The increase in elasticity is for example an increase of at least 15% of the slope alpha relative to the slope alpha measured before application of the extract according to the invention, using a method of ballistometry on dermis equivalents containing fibroblasts and dermal stem cells of the SKP or SKP-like type, in particular according to the protocol of example 6.

The increase in cellular renewal of the skin may be an increase in expression of at least one of the markers Nestin, OCT4 and SOX2 in fibroblasts, measured by a method of quantitative PCR, by comparing the amount of mRNA of SOX2, Nestin and/or OCT4 expressed by fibroblasts cultured in vitro, before and after application of the extract of the invention, used in an amount equivalent to a dry weight of the order of 0.01 wt % of the weight of culture medium. The increases in the expression of mRNA of SOX2, Nestin and OCT4 in fibroblasts are preferably at least 250%, at least 100% and at least 250%, respectively.

The invention also relates to a method of cosmetic care consisting of applying a synergistic extract as described above on a subject's healthy skin, to increase the firmness, flexibility and/or elasticity of the skin, or to increase its rate of renewal.

The embodiments that are specific to these methods of cosmetic care and to these uses also result from the above description.

Other advantages and features of the invention may be seen in more detail on reading the illustrative, nonlimiting examples given hereunder.

In all the figures, the numerical values that have been used for graphical representation are the mean values of three measurements. The error bars correspond to the calculated values RQmin and RQmax, based on the mean standard deviation: *: Highly significant; : Very significant, *: Significant in Dunnett's test.

FIG. 1: qPCR of the mRNAs of SOX2, Nestin and OCT4 after application of different extracts on fibroblasts. The numerical values used for graphical representation are the mean values of three measurements. The error bars correspond to the calculated values RQmin and RQmax, based on the mean standard deviation: *: Highly significant; : Very significant, *: Significant in Dunnett's test.

Figure 2:
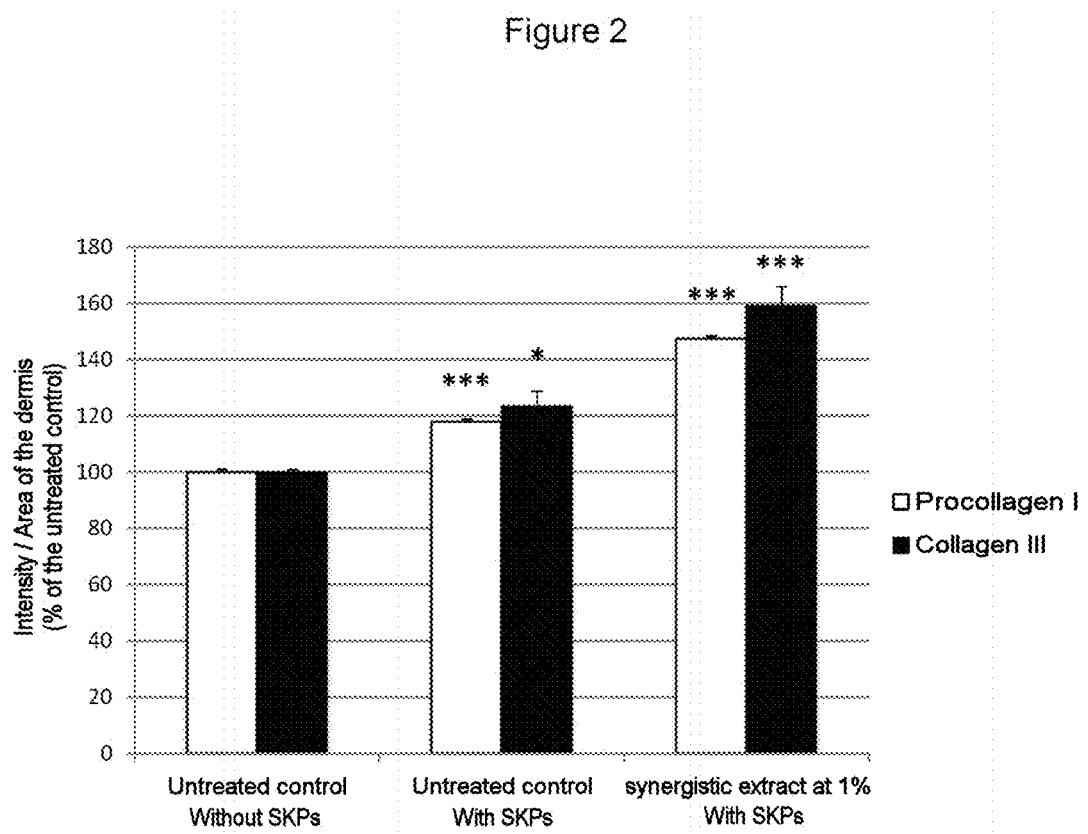
FIG. 2 is a chart showing expression of the neo-synthesized proteins of collagen I and collagen III from Example 3.

FIG. 2: Expression of proteins of the extracellular matrix (procollagen I and collagen III) after application of 1% of the synergistic extract according to example 1 on dermis equivalent containing SKP cells. The numerical values used for graphical representation are the mean values of three measurements. The error bars correspond to the calculated values RQmin and RQmax, based on the mean standard deviation: *: Highly significant; : Very significant, *: Significant in Dunnett's test.

Figure 3:
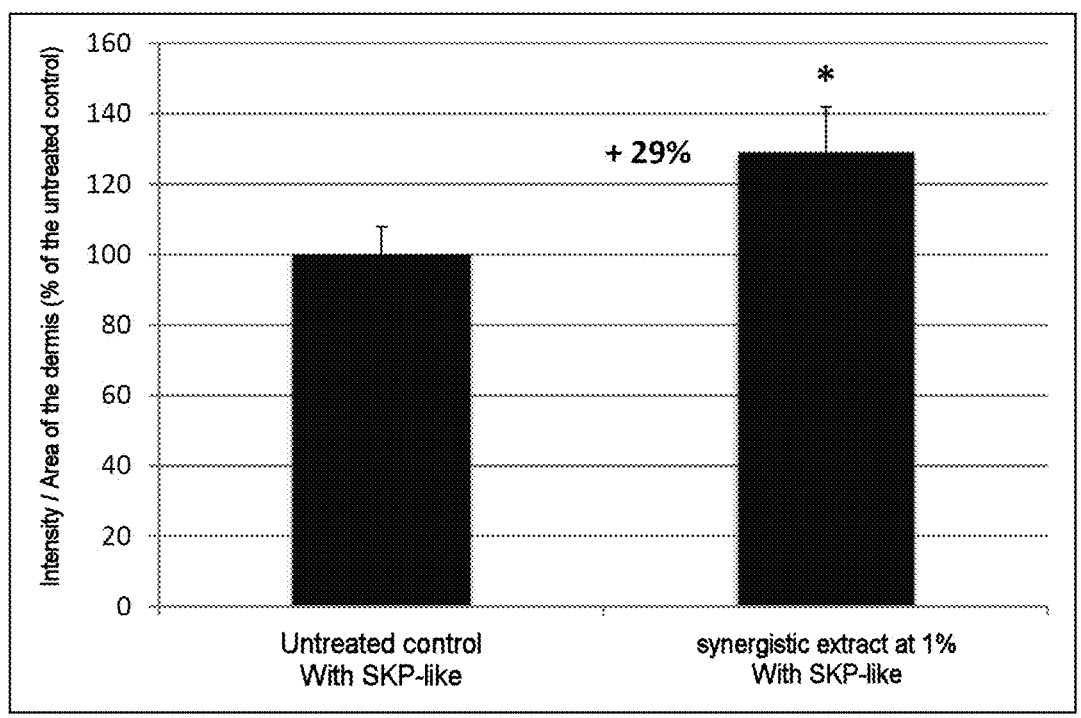
FIG. 3 is a chart showing expression of the proteins of collagen III from Example 4.

FIG. 3: Expression of collagen III after application of 1% of the synergistic extract according to example 1 on dermis equivalent containing SKP-like cells. (mean+/−SEM; n=6, 3 dermis per condition and 2 photographs per dermis equivalent). *: Significant in Student's "t" test—one-sided hypothesis.

Figure 4:
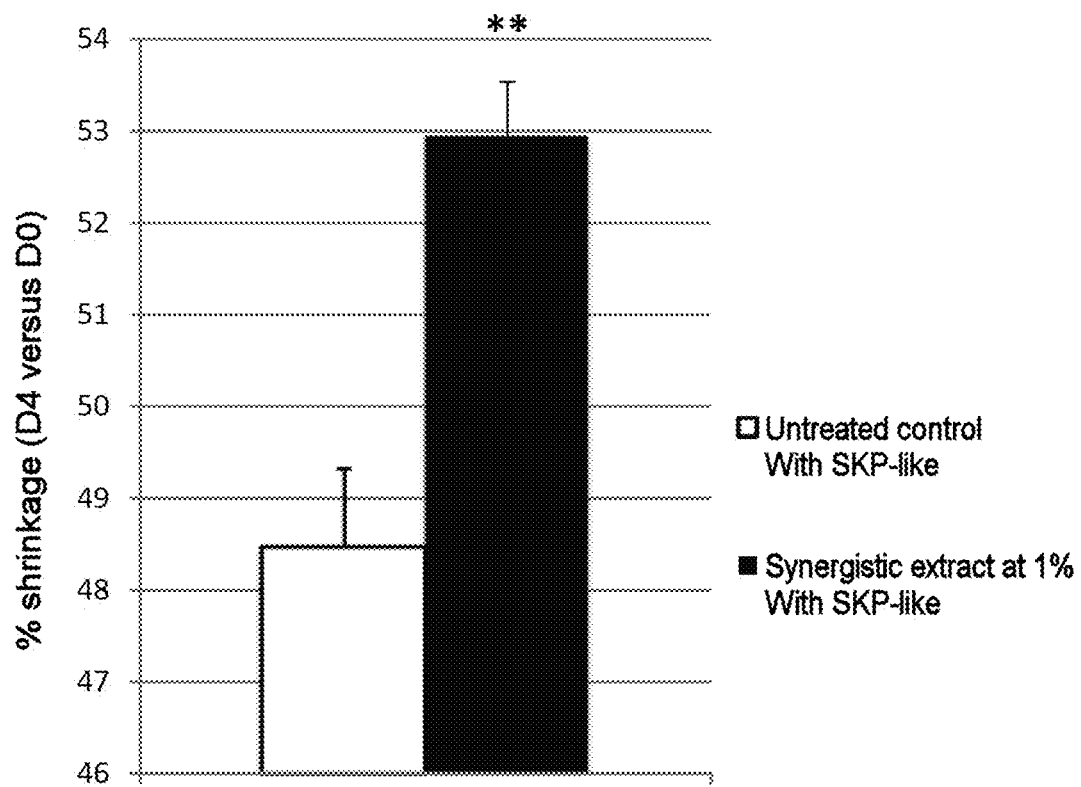
FIG. 4 is a chart showing the diameter of dermis equivalents from Example 4.

FIG. 4: Measurement of the shrinkage of the dermis equivalents containing SKP-like cells, after application of 1% of the synergistic extract according to example 1. (mean+/−SEM; n=3 dermis equivalent). **: Very significant in Student's "t" test—one-sided hypothesis.

Figure 5:
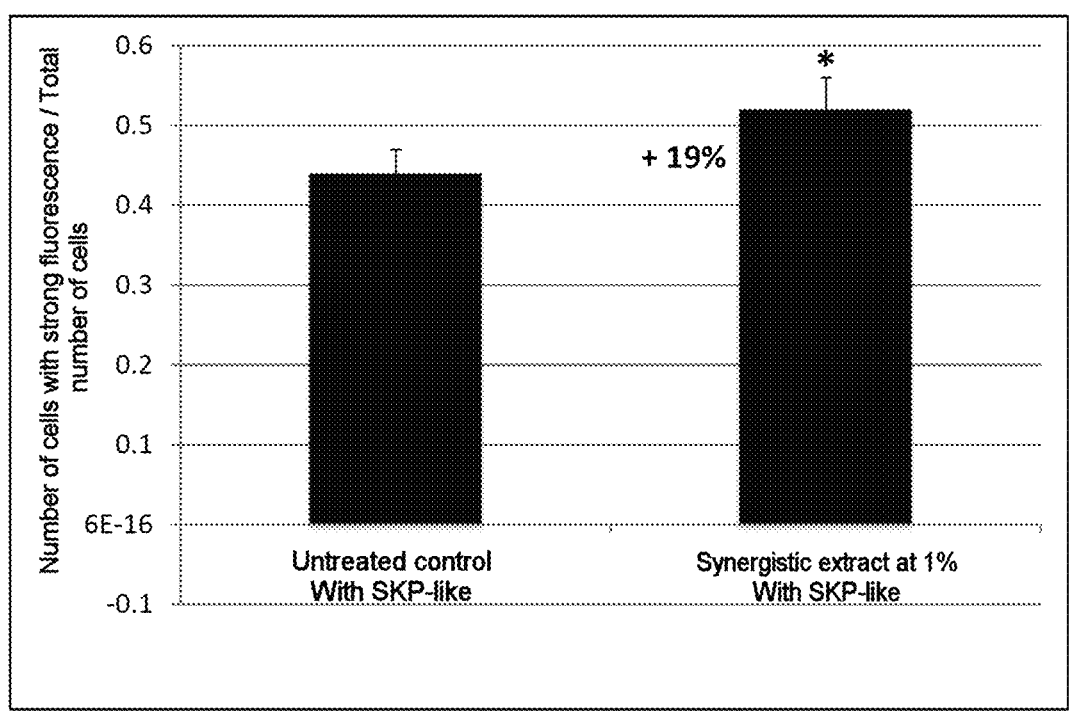
FIG. 5 is a chart showing synthesis of tropoelastin fibers from Example 5.

FIG. 5: Measurement of the synthesis of tropoelastin fibers in dermis equivalents containing SKP-like cells, after application of 1% of the synergistic extract according to example 1. (mean+/−SEM; n=10-12, 3-4 photographs per dermis equivalents). *: Significant in Student's "t" test—one-sided hypothesis.

Figure 6:
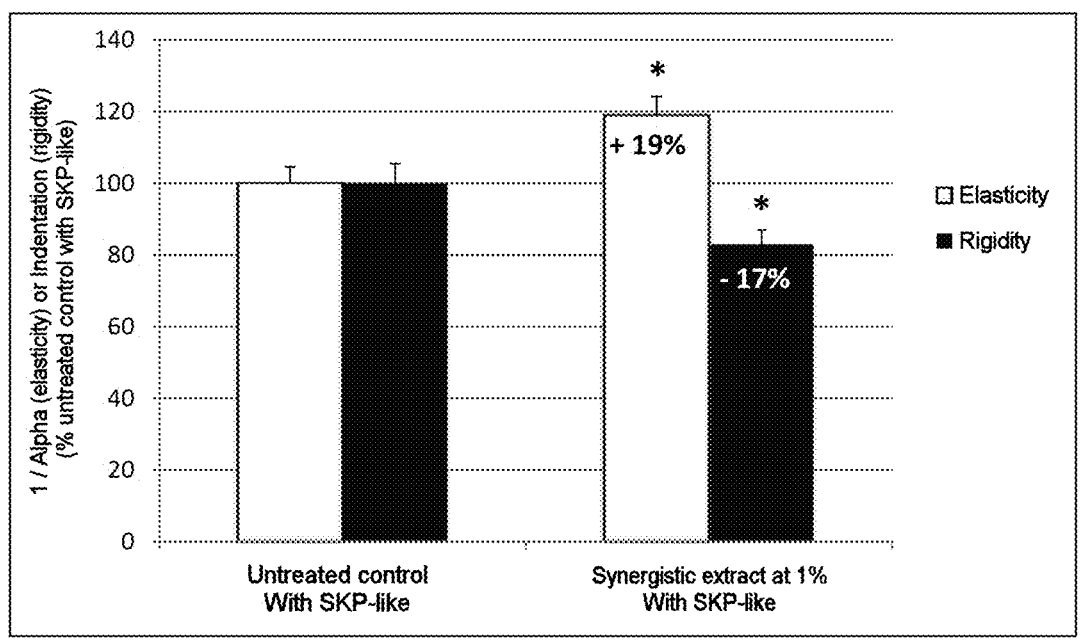
FIG. 6 is a chart showing elasticity and rigidity of the dermis from Example 6.

FIG. 6: Measurement of the rigidity and elasticity of the dermis equivalents containing SKP-like cells, after application of 1% of the synergistic extract according to example 1. (mean+/−SEM; n=15, 5 measurements per dermis equivalents). *: Significant in Student's "t" test—one-sided hypothesis.

Figure 7:
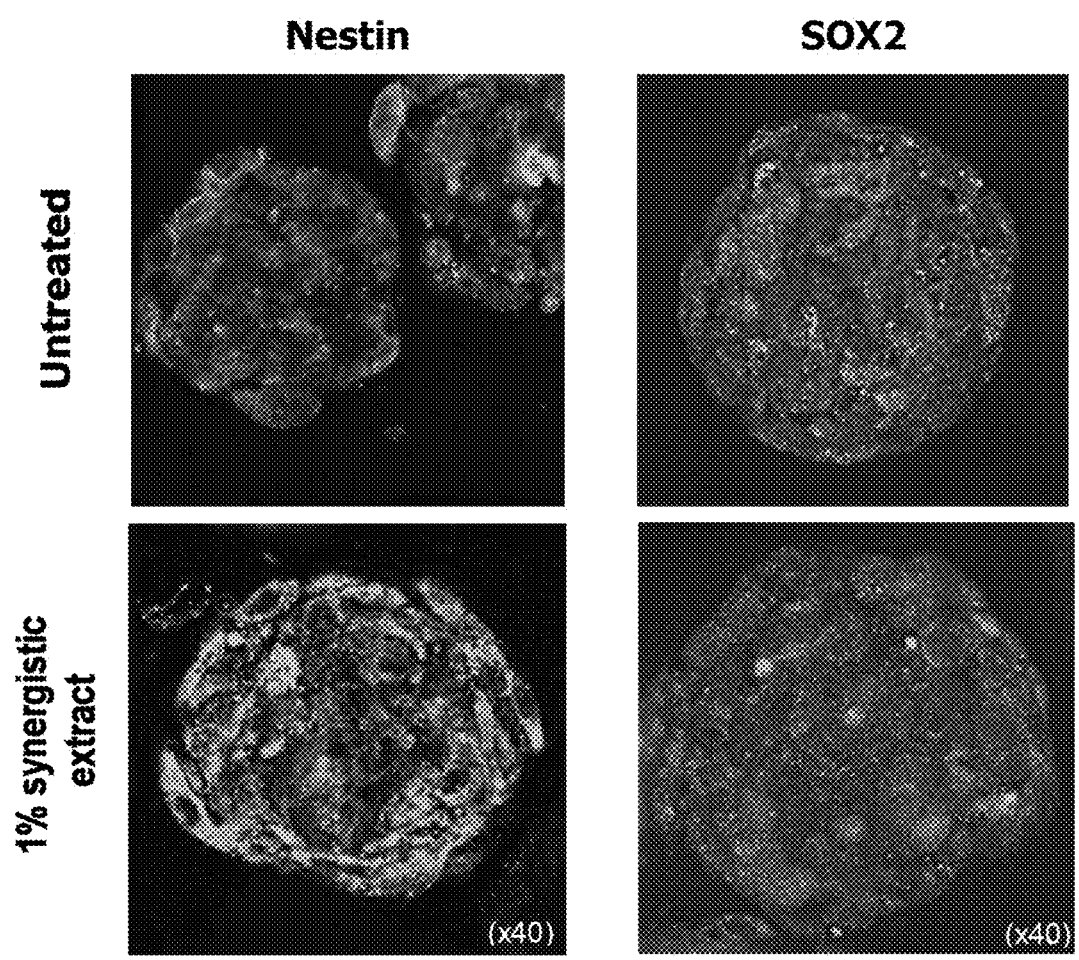
FIG. 7 shows microscopy images from immunolabeling for SOX2 and Nestin in Example 8.

FIG. 7: Photograph of the observations by light microscopy (magnification *40) before and after activation of the markers SOX2 and nestin, by the synergistic extract from example 1.

All the results expressed in the following examples are statistically significant according to Student's or Dunnett's test ($p<0.05$).

EXAMPLE 1

Preparation of a Synergistic Extract of *Palmaria palmata* and of Jasmine Flower Heads 180 g of *Palmaria palmata* in the form of flakes is dissolved in 4 kg of water and the pH is adjusted to a value between 4.5 and 5.5 with HCl.

In order to extract the sugars from *Palmaria palmata*, hydrolysis is performed using a hydrolase and a protease. For this, 7.2 g of xylanase and 3.6 g of bromelain are added to the reaction mixture. The reaction mixture is then heated for two hours at 55° C.

A filtration step makes it possible to discard the solid residue and only keep the carbohydrate-rich filtrate. For this, 10 g/kg of CELATOM® (filter aid) is added and the solution is centrifuged for 10 minutes at 4000 rev/min. After centrifugation, the residual solid is removed and the filtrate is then clarified to a varying extent by filtration on a cellulose filter.

In a second step, 20 g of flowers of *Jasminum officinale* are added to the filtrate of about 3.6 kg obtained, and maceration is carried out for 2 hours at ambient temperature.

10 g/kg CELATOM® is added to the mixture and the solid is separated from the filtrate by filtration.

The filtrate (resulting from enzymatic hydrolysis of *Palmaria palmata* and maceration of jasmine flower heads) is then heated overnight at 80° C. to deactivate the residual enzymes.

The solution is then purified by filtration with filters of decreasing porosity, obtaining a bright, amber-colored clear solution.

The synergistic extract obtained is characterized by dry matter of 28.8±2.0 g/kg, a protein content of 1.8±0.5 g/kg and a content of sugars of 27.3±2.0 g/kg.

The solution is then diluted with water and filtered in sterile conditions, and then pasteurized at low temperature (65° C. overnight) to complete the sterilization.

The end product corresponding to the active synergistic extract is a clear solution, of pale yellow color, characterized by: dry matter of 10±3.0 g/kg, a content of sugars between 8 and 12 g/kg and a pH between 4 and 5.

EXAMPLE 2

Evaluation of the mRNAs of SOX2, Nestin and OCT4 After Application of a Synergistic Extract Obtained According to Example 1, Compared to a Reference Extract of *Palmaria palmata*, and a Reference Extract of Jasmine Flower Heads The purpose of this study is to compare the amount of mRNA of SOX2, of Nestin and of OCT4 expressed by the cells after treatment with a reference extract of jasmine, with a reference extract of *Palmaria palmata* and with the synergistic extract obtained according to example 1.

The level of mRNA of SOX2, Nestin or OCT4 was evaluated by quantitative PCR (q-PCR).

An extract derived from jasmine flower heads alone and an extract derived from *Palmaria palmata* alone were also prepared with the aim of carrying out comparative tests of biological efficacy.

Care was taken to prepare the reference extracts and the synergistic extract in the same conditions (same level of dry plant material/kg of water, same pH, same conditions of filtration and clarification).

Preparation of a Reference Extract of Jasmine:

20 g of dried flower heads of *Jasminum officinale* are put in 1 kg of water and macerated for 2 h at ambient temperature with stirring. Then successive filtrations using filters of decreasing porosity (20-50 µm down to 0.3-0.5 µm) are performed in order to discard the solid residues and clarify the extract.

The extract obtained is characterized by dry matter of 5±0.5 g/kg. Next, the extract was diluted in water to a final concentration of 3±0.5 g/kg dry matter. The pH is adjusted to 4. The extract is then submitted to sterilizing filtration on a 0.2 µm filter and left at 65° C. overnight for low-temperature pasteurization in order to complete the sterilization.

Preparation of a Reference Extract of *Palmaria palmata*:

50 g of *Palmaria palmata*, in the form of flakes, is dissolved in 1 kg of water. Hydrolysis is carried out using 2 g of xylanase and 1 g of bromelain, added to the reaction mixture. The reaction mixture is then heated for two hours at 55° C. A filtration step makes it possible to discard the solid residue and only keep the carbohydrate-rich filtrate. For this, 10 g/kg Celatom® (centrifugation aid) is added and the solution is centrifuged for 10 minutes at 4000 rev/min. After centrifugation, the residual solid is discarded and the supernatant is then clarified by filtration on filters of decreasing porosity, down to a porosity of 7-20 µm, and kept at 80° C. overnight. The next day the extract is filtered again on filters of decreasing porosity, down to 0.3-0.5 µm. The extract obtained is characterized by dry matter of 30±2 g/kg. Then the extract is diluted in water to give 20±2 g/kg dry matter. The pH is then adjusted to 4-4.5.

The extract is then submitted to sterilizing filtration on a 0.2 µm filter and kept at 65° C. overnight for low-temperature pasteurization to complete the sterilization.

Protocol for evaluation of the mRNAs: Normal human fibroblasts are treated with the various extracts prepared previously and diluted to 1% vol/vol in the culture medium ( ). In parallel, cultures of fibroblasts are left without treatment, to constitute an untreated control. Culture takes place at 37° C. in a humidified atmosphere containing 5% $CO_2$.

At the end of this incubation, the total RNAs are extracted with the RNeasy mini kit (QIAGEN, 74104) and reverse-transcribed with the High Capacity cDNA reverse-transcription kit containing inhibitors of RNAses (Applied Biosystems, 4368814). Quantitative PCR is performed using the Step One Plus thermocycler (Applied Biosystems). The primers and probes of the targets SOX2, Nestin and OCT4 as well as those of the endogenous control 18S are obtained from Taqman Expression Assays (Applied Biosystems, Hs99999901_s1 for 18S; Hs01053049_s1 for SOX2, Hs00707120_s1 for Nestin and Hs00999632_g1 for OCT4), diluted in sterile water and Master Mix (Applied Biosystems).

Results:

The results, as presented in FIG. 1, show a statistically significant increase of 29%, 26% and 34% in expression of the mRNAs of SOX2, Nestin and OCT4 respectively in the fibroblasts treated with 1% of the reference extract of *Palmaria palmata*, compared to the untreated control.

No stimulation was observed with the extract of jasmine alone.

In the case when the fibroblasts were treated with the synergistic extract obtained according to example 1 at 1%, the results show that the increases are substantially greater than those observed previously with the extract of *Palmaria palmata*, of 296% for expression of the mRNAs of SOX2, 123% for expression of the mRNAs of Nestin and 285% for expression of the mRNAs of OCT4, respectively, compared to the untreated control.

Conclusion:

A higher level of mRNA of SOX2, Nestin and OCT4 is observed in the fibroblasts pretreated with the synergistic extract obtained according to example 1, compared to the untreated control cells, the reference extract of jasmine and the reference extract of alga. The synergistic extract obtained according to example 1 gives a synergistic increase in the markers characteristic of the "stem" character of the dermal cells.

EXAMPLE 3

Demonstration of the Activating Effect of the Synergistic Extract Obtained According to Example 1 on Expression of Procollagen I and Collagen III, in Dermis Equivalents Containing Human Fibroblasts and SKP Cells The purpose of this study is to determine the effect of the synergistic extract obtained according to example 1 on expression of the following proteins of the extracellular matrix: procollagen I and collagen III.

For this, specific labeling was performed starting from reconstructed dermis equivalents consisting of polymerized bovine collagen I, human fibroblasts and SKP stem cells.

Immunolabeling protocols: Human fibroblasts were extracted from adult donor skin explants. The SKP cells used in this experiment are obtained from foreskin. The SKP cells in culture are pretreated twice a day with the extract according to example 1 diluted to 1/100 in culture medium (i.e. 1% vol/vol), for 7 days. As the extract obtained in example 1 has a dry weight of about 10 g/kg, the extract is tested at about 0.01 wt % of the weight of culture medium. In this model, the stem cells are stimulated with the extract prior to incorporation in the dermal equivalents, in order to be sure of a direct effect of the extract. In parallel, cultures of SKP cells are maintained without treatment, so as to constitute an untreated control of SKP cells. Culture takes place at 37° C. in a humidified atmosphere containing 5% $CO_2$.

The dermis equivalents were prepared by mixing a solution of type I bovine collagen, to which the SKP cells, cultured in the form of spheres, and the fibroblasts suspended in culture medium in a respective proportion of 1 sphere of SKP cells to 10000 fibroblasts, are added. The mixture is carefully homogenized and distributed in the wells of a 6-well plate. Polymerization of the collagen I takes place, allowing formation of dermis equivalents. The dermis equivalents are treated twice a day with the synergistic extract obtained according to example 1, at a concentration of 1% relative to the volume of the mixture, for 5 days and maintained at 37° C. in a humidified atmosphere containing 5% $CO_2$.

The samples are fixed with 10% paraformaldehyde and embedded in paraffin after a succession of baths of ethanol and xylene (Shandon).

Immunolabeling is performed on sections with a thickness of 4 μm.

For procollagen I, the tissues are submitted to microwave unmasking at 600 W in 0.01M citrate buffer pH6 (Sigma), followed by enzyme treatment with pepsin 0.25% (15 min at 37° C.; Zymed, Invitrogen).

Regarding the treatment of tissue sections for collagen III immunolabeling, microwave unmasking at 600 W is performed, followed by enzyme treatment with 0.5% trypsin (15 min at 37° C., Zymed, Invitrogen).

After 30 min of saturation, the sections are incubated in the presence of a rat monoclonal antibody specific to procollagen I (Millipore), a rabbit polyclonal antibody specific to collagen III (Rockland), and then an anti-rat secondary antibody coupled to a fluorochrome (Invitrogen) or anti-rabbit coupled to a fluorochrome (Invitrogen). The sections of dermis equivalents are then examined with the epifluorescence microscope (Nikon Eclipse 80i microscope).

Three photographs per condition are analyzed quantitatively with the Volocity image analysis software (Improvision).

The statistical analyses are performed with JMP software (SAS).

Results:

The results, as presented in FIG. 2, showed a significant increase of 18%, and 23% in expression of the neo-synthesized proteins of collagen I and of collagen III in the untreated dermis equivalents containing SKP cells, relative to the untreated control, not containing SKP cells.

Treatment of the samples of dermis equivalents containing the SKP cells with 1% of the synergistic extract obtained according to example 1 caused increases of 25% and 29% of procollagen I and collagen III respectively, compared to the untreated control with SKP cells.

Conclusions:

Application of 1% of the synergistic extract obtained according to example 1 in dermis equivalents containing the SKP dermal stem cells stimulates expression of procollagen I and collagen III.

EXAMPLE 4

Demonstration of the Activating Effect of the Synergistic Extract Obtained According to Example 1 on Skin Shrinkage and Expression of Collagen III, in Dermis Equivalents Containing Human Fibroblasts and SKP-like Cells Wenzel et al. (*Biology Open*. 1:516-526, 2012) and Hill et al. (*Plos One*, November 2012, Vol. 7, Issue 11, e50742) have demonstrated that SKP-like cells could be isolated after cold stress applied in vitro on adult donor fibroblasts.

The purpose of this study is to determine the effect of the synergistic extract obtained according to example 1 on the shrinkage of dermis equivalents and on expression of collagen III in dermis equivalents of collagen containing fibroblasts and SKP-like cells obtained from the same donor.

Shrinkage of the dermis equivalents is a process associated with the contractile activity of the fibroblasts, which bond to the collagen microfibrils, orient them in one and the same direction and densify the extracellular matrix. The diameter stabilizes after a few days. Immunolabeling was performed starting from reconstructed dermis equivalents to monitor the synthesis of the specific proteins of the extracellular matrix.

Protocol: Human fibroblasts were extracted from an adult donor skin explant. A portion of these fibroblasts in culture was submitted to cold stress (4° C., overnight) in order to generate SKP-like cells. The cells having the same characteristics as the SKP cells thus obtained are called "SKP-like" here. The SKP-like cells used in this experiment are treated twice a day with the synergistic extract obtained according to example 1 diluted to 1/100 in culture medium (i.e. 1% vol/vol), for 6 days. In parallel, SKP-like cultures are maintained without treatment, so as to constitute an untreated SKP-like control. Culture takes place at 37° C. in a humidified atmosphere containing 5% $CO_2$.

The dermis equivalents were prepared with a mixture of type I bovine collagen, to which the SKP-like cells, cultured in the form of multicellular spheres, are added. The SKP-like cells and the fibroblasts were included in a proportion of 1 sphere to 10000 fibroblasts. The matrix mixture of collagen I/cells is distributed in wells of a 6-well plate. The dermis equivalents, once polymerized, are cultured floating in the medium. The dermis equivalents are treated twice a day with the synergistic extract obtained according to example 1, at a concentration of 1%, for 5 days and maintained at 37° C. in a humidified atmosphere containing 5% $CO_2$. As the extract from example 1 has a dry weight of about 10 g/kg, the extract is tested at about 0.01 wt % of the weight of culture medium.

Each day, for 3 dermis equivalents per condition, the skin shrinkage, which is reflected in a decrease in diameter of the dermis equivalents, is monitored by taking photographs in culture, and then quantified using image analysis software (Image J).

On completion of culture, the tissues are fixed with 10% paraformaldehyde and embedded in paraffin after a succession of baths of ethanol and xylene (Shandon).

Immunolabeling was performed on sections with a thickness of 4 μm.

For collagen III, the sections underwent microwave unmasking followed by enzyme treatment with trypsin 0.5% (15 min at 37° C., Zymed, Invitrogen). After 30 min of saturation, the sections are incubated in the presence of a rabbit polyclonal antibody specific to collagen III (Rockland), and then an anti-rabbit secondary antibody coupled to a fluorochrome (Invitrogen). The sections of dermis equivalents are then examined with the epifluorescence microscope (Nikon Eclipse 80i microscope).

Three photographs per condition are analyzed with the Volocity image analysis software (Improvision).

The statistical analyses are performed with JMP software (SAS).

Results: The results, as presented in FIG. 3, showed a significant increase of 29% in expression of the proteins of collagen III in the dermis equivalents treated with 1% of the synergistic extract obtained according to example 1, compared to the untreated control with SKP-like cells.

Analysis of the diameter of the dermis equivalents, as presented in FIG. 4, showed a very significant increase in the contractility of the dermis equivalent after 4 days of treatment with the synergistic extract obtained according to example 1, compared to the untreated control with SKP-like cells.

Conclusions: Application of 1% of the synergistic extract obtained according to example 1 in dermis equivalents containing the dermal "stem" cells (SKP-like cells) obtained from adult donor fibroblasts improves the contractility of the tissue and stimulates expression of collagen III.

EXAMPLE 5

Demonstration of the Activating Effect of the Synergistic Extract Obtained According to Example 1 on the Synthesis of Tropoelastin Fibers, in Dermis Equivalents Containing Human Fibroblasts and SKP-like Cells The purpose of this study is to determine the effect of the synergistic extract obtained according to example 1 on the synthesis of tropoelastin fibers in dermis equivalents of collagen containing fibroblasts and SKP-like cells obtained from the same donor. Immunolabeling was performed starting from reconstructed dermis equivalents to monitor the synthesis of tropoelastin fibers starting from fibroblasts.

Protocol: Dermis equivalents of collagen containing fibroblasts and SKP-like cells obtained from the same donor were prepared following the same protocol as specified in example 5, apart from the treatments. In fact, the SKP-like cells used in this experiment are treated twice a day with the synergistic extract obtained according to example 1 diluted to 1/100 in culture medium (i.e. 1% vol/vol), for 5 days. The dermis equivalents are treated twice a day with the synergistic extract obtained according to example 1 at a concentration of 1%, for 6 days. As the extract obtained in example 1 has a dry weight of about 10 g/kg, the extract is tested at about 0.01 wt % of the weight of culture medium.

On completion of culture, the tissues are fixed with 10% paraformaldehyde and embedded in paraffin after a succession of baths of ethanol and xylene (Shandon).

Immunolabeling was performed on sections with a thickness of 4 μm.

The sections underwent unmasking by enzyme treatment with 0.5% trypsin (15 min at 37° C., Zymed, Invitrogen). After 30 min of saturation, the sections are incubated in the presence of a rabbit polyclonal antibody specific to tropoelastin (Abcam), then an anti-rabbit secondary antibody coupled to a fluorochrome (Invitrogen). The sections of dermis equivalents are then examined with the epifluorescence microscope (Nikon Eclipse 80i microscope).

Ten to twelve photographs per condition are analyzed. The number of cells with strong fluorescence and the total number of cells are counted.

The statistical analyses are performed with JMP software (SAS).

Results: The results, as presented in FIG. 5, showed a significant increase of 19% in synthesis of tropoelastin fibers in the dermis equivalents treated with 1% of the synergistic extract obtained according to example 1, compared to the untreated control with SKP-like cells.

Conclusions: Application of 1% of the synergistic extract obtained according to example 1 in dermis equivalents containing the dermal "stem" cells (SKP-like cells) obtained from adult donor fibroblasts improves the synthesis of the elastic fibers.

EXAMPLE 6

Demonstration of the Activating Effect of the Synergistic Extract Obtained According to Example 1 on the Elastic Properties of the Dermis Equivalents Containing Human Fibroblasts and SKP-like Cells The purpose of this study is to determine the effect of the synergistic extract obtained according to example 1 on the elastic properties of dermis equivalents of collagen containing fibroblasts and SKP-like cells obtained from the same donor. The reference ballistometer BLS780 (Monaderm) is an apparatus for determining the elasticity and rigidity of the skin. It is supplied with software that parametrizes the measurements automatically.

Protocol: Dermis equivalents of collagen containing fibroblasts and SKP-like cells obtained from the same donor were prepared following the same protocol as specified in example 4, apart from the treatments. In fact, the SKP-like cells used in this experiment are treated twice a day with the synergistic extract obtained according to example 1 diluted to 1/100 in culture medium (i.e. 1% vol/vol), for 5 days. The dermis equivalents are treated twice a day with the synergistic extract obtained according to example 1 at a concentration of 1%, for 10 days). As the extract obtained in example 1 has a dry weight of about 10 g/kg, the extract is tested at about 0.01 wt % of the weight of culture medium.

Methodology: A probe is placed on the dermis equivalent. A ball is released from the probe and penetrates with a constant force, predetermined by the apparatus, and bounces on the surface of the skin. It then performs several oscillations before stabilizing. The depth of penetration of the ball when released (called indentation) makes it possible to measure the rigidity of the skin. In fact, the deeper the indentation made by the ball, the softer the tissue, and therefore it has lower rigidity. The second criterion is the slope of the curve joining all the tops of the peaks (called alpha), which allows the elasticity of the skin to be determined. In the case of skin with good elasticity, the ball bounces more and therefore the slope has a lower value.

Results: The results, as presented in FIG. 6, showed a significant increase of 19% in the elasticity of the dermis equivalents treated with 1% of the synergistic extract obtained according to example 1, compared to the untreated control with SKP-like cells. In parallel, a significant decrease of 17% in the rigidity of the dermis equivalents was observed compared to the control.

Conclusions: Application of 1% of the synergistic extract obtained according to example 1 in dermis equivalents containing the dermal "stem" cells (SKP-like cells) obtained from adult donor fibroblasts improves the elastic properties and the flexibility of dermis equivalents.

EXAMPLE 7

Examples of Cosmetic Compositions Containing the Synergistic Extract of the Invention

A—SERUM

| Ingredients (Trade name/INCI) | | % w/w | Supplier |
|---|---|---|---|
| Phase A | | | |
| Purified Water | Water/Aqua | Qs. 100 | |
| Pemulen* TR-2 | Acrylates/C10-30 Alkyl Acrylate Crosspolymer | 0.30 | Lubrisol |
| Optiphen ™ preservative | Phenoxyethanol (and) Caprylyl Glycol | 1.50 | Ashland |
| Methylparaben preservative | Methylparaben | 0.20 | Ashland |
| Phase B | | | |
| Ceraphyl ™ 230 ester | Diisopropyl Adipate | 2.00 | Ashland |
| Ceraphyl SLK ester | Isodecyl Neopentanoate | 4.00 | Ashland |
| Cerasynt ™ 945 ester | Glyceryl Stearate (and) Laureth-23 | 1.00 | Ashland |
| Ceteareth-20 | Ceteareth-20 | 2.00 | |
| Refined Shea Butter | *Buty rospermum Parkii* (Shea) Butter | 1.50 | Ashland |
| Phase C | | | |
| Triethanolamine | Triethanolamine | 0.20 | |
| Purified Water | Water/Aqua | 5.00 | |
| Phase D | | | |
| Si-Tec ™ RE-100 | Cyclopentasiloxane (and) Dimethicone/Vinyltrimethylsiloxysilicate | 3.00 | Ashland |
| Lubrajel* II XD hydrogel | Water/Aqua (and) Glycerin (and) Glyceryl Polyacrylate | 2.00 | Ashland |
| CM 1000 | Cyclopentasiloxane (and) Dimethiconol | 2.00 | Wacker-Belsil |
| Synergistic extract according to example 1 | | 1.50 | Ashland |
| BPD 500* | HDI/Trimethylol Hexyllactone Crosspolymer (and) Silica | 0.50 | Kobo Products |
| Total | | 100.00 | |

Protocol for Preparation:

Add water to the main container. Heat under gentle homogenization.

Pour the Pemulen TR-2 slowly into the water and mix until completely rehydrated.

Maintain the temperature between 70° and 75° C.

When the polymer is completely mixed, without any lumps, add the preservatives one by one, with mixing.

In a second container, mix Phase B and heat to 75° C.

Add Phase B to the main container, while homogenizing.

Cool to 60-65° C. and add the premixed Phase C.

Cool to 40-45° C. and add the ingredients of Phase D, one by one, mixing between each addition.

Cool with stirring to room temperature (25° C.).

B—Night Cream

| Ingredients (Trade name | INCI) | % w/w | Supplier |
|---|---|---|---|
| Phase A | | | |
| Purified Water | Water/Aqua | Qs. 100 | |
| Versene* NA2 | Disodium EDTA | 0.10 | Dow |
| Bulylene Glycol | Butylene Glycol | 3.00 | |
| Glycerin | Glycerin | 1.00 | |
| Phase B | | | |
| Arlacel* 165 | Glyceryl Stearate (and) PEG-100 Stearate | 4.80 | Croda |
| Behenyl Alcohol | Behenyl Alcohol | 1.50 | |
| Cetyl Alcohol | Cetyl Alcohol | 2.50 | |
| Lanette* 18 | Stearyl Alcohol | 1.00 | BASF |
| Ceraphyl™ 375 ester | Isostearyl Neopentanoate | 2.00 | Ashland |
| Ceraphyl 494 ester | Isocetyl Stearate | 5.00 | Ashland |
| Ceraphyl 368 ester | Ethylhexyl Palmitate | 2.40 | Ashland |
| ProLipid™ 141 lamellar gel | Glyceryl Stearate (and) Behenyl Alcohol (and) Palmitic Acid (and) Stearic Acid (and) Lecithin (and) Lauryl Alcohol (and) Myristyl Alcohol | 1.00 | Asland |
| Dow Corning 200 Fluid-100 cst* | Dimethicone | 0.50 | Dow Corning |
| Floraesters 70 | Jojoba Esters | 0.50 | Floratech |
| Phase C | | | |
| Carbopol* 940 Polymer | Carbomer | 0.30 | Lubrisol |
| Phase D | | | |
| TEA 99% | Triethanolamine | 0.30 | |
| Purified Water | Water/Aqua | 5.00 | |
| Phase E | | | |
| LiquaPar™/Rokonsal™ Optima preservative | Phenoxyethanol (and) methylparaben (and) isopropylparaben (and) butylparaben (and) Isobutylparaben | 1.00 | Ashland |
| Synergistic extract according to example 1 | | 3.00 | Ashland |
| Phase F | | | |
| BPD 500* | HDI/Trimethylol Hexyllactone Crosspolymer (and) silica | 0.25 | Kobo Product |
| Flamenco Satina* | Mica (and) Titanium Dioxide | 0.50 | BASF |
| FD&C Red 40 07700-C (Sol. 0.1%) | Water/Aqua (and) CI 16035 (Red 40) | 0.20 | |
| Total | | 100.00 | |

Protocol:

Add water to the main container with gentle homogenization. Add the rest of the ingredients of Phase A one by one and heat to 70-75° C. while mixing.

In a 2nd container, mix the ingredients of Phase B and heat to 75° C. while mixing.

Add Phase B (70-75° C.) to Phase A (70-75° C.) while stirring vigorously (10 minutes).

Begin to cool.

At 60-65° C., sprinkle Phase C into the mixture. Mix well to obtain complete hydration of the polymer (optionally increase the mixing speed).

Premix Phase D; add to the mixture and mix the whole carefully to obtain a uniform mixture. The mixture becomes thicker. Continue to cool.

Cool to 40° C., stirring slowly. Add the ingredients of phase E one by one, stirring well between each addition.

At room temperature, add Phase F. Mix well. Stop at 25° C.

C—Detoxifying Cream

| Ingredients (Trade name INCI) | | % w/w | Supplier |
|---|---|---|---|
| Phase A | | | |
| Purified Water | Water/Aqua | Qs. 100 | |
| Versene* Na2 | Disodium EDTA | 0.10 | Dow |
| Phase B | | | |
| Arlacel* 165 | Glyceryl Stearate (and) PEG-100 Stearate | 4.00 | Croda |
| Lanette* 16 | Cetyl Alcohol | 1.50 | BASF |
| Ceraphyl™ 375 ester | Isostearyl Neopentanoate | 2.00 | Ashland |
| Ceraphyl 230 ester | Diisopropyl Affiliate | 4.00 | Ashland |
| Ceraphyl 368 ester | Ethylhexyl Palmitate | 3.00 | Ashland |
| ProLipid™ 141 lamellar gel | Glyceryl Stearate (and) Behenyl Alcohol (and) Palmitic Acid (and) Stearic Acid (and) Lecithin (and) Lauryl Alcohol (and) Myristyl Alcohol (and) Cetyl Alcohol | 0.50 | Ashland |
| Phase C | | | |
| RapiThix™ A-60 polymer | Sodium Polyacrylate (and) Hydrogenated Polydecene (and) Trideceth-6 | 1.00 | Ashland |
| Lubrajel* II XD hydrogel | Water/Aqua (and) Glycerin (and) Glyceryl Polyactylate | 2.50 | Ashland |
| Phase D | | | |
| Germaben™ II preservative | Propylene Glycol (and) Diazolidinyl Urea (and) Methylparaben (and) Propylparaben | 1.00 | Ashland |
| Prolixir S20™ biofunctional | Water (and) Butylene Glycol (and) Dimer Tripeptide-43 | 1.00 | Ashland |
| Synergistic extract according to example 1 | | 1.00 | Ashland |
| Total | | 100.00 | |

Protocol:

Add water to the main container with gentle homogenization. Add the Versene and mix until completely dissolved. Heat to 70-75° C.

In a 2nd container, mix the ingredients of Phase B and heat to 70° C.-75° C. while mixing.

At 75° C., add Phase B to Phase A under strong for 10 minutes. Begin to cool.

Cool to 60-65° C. and add the ingredients of Phase C one by one, mixing between each addition.

Cool to 40-45° C. and add the ingredients of Phase D, one by one, mixing between each addition.

Cool while stirring slowly to room temperature. Stop at 25° C.

EXAMPLE 8

Demonstration of the Activating Effect of the Synergistic Extract Obtained According to Example 1 on Protein Expression of the Markers SOX2, OCT4 and Nestin in SKP-like Cells The purpose of this study is to determine the effect of the synergistic extract obtained according to example 1 on expression of proteins that are characteristic of the stem cells: SOX2, OCT4 and nestin.

For this, specific labeling was performed on pellets of SKP-like cells embedded in paraffin.

Immunolabeling protocols: SKP-like cells were isolated from human fibroblasts extracted from adult donor skin explants. The SKP-like cells are treated twice a day with the extract according to example 1 diluted to 1/100 in culture medium (i.e. 1% vol/vol), for 2 days. As the extract obtained in example 1 has a dry weight of about 10 g/kg, the extract is tested at about 0.01 wt % of the weight of culture medium. Culture takes place at 37° C. in a humidified atmosphere containing 5% $CO_2$.

At the end of culture, the SKP-like cells are prepared as a cellular pellet, fixed with 10% paraformaldehyde and embedded in paraffin after a succession of baths of ethanol and xylene (Shandon).

Immunolabeling is performed on sections with a thickness of 4 µm.

For the three immunolabelings, the sections are submitted to microwave unmasking at 600 W in 0.01M citrate buffer pH6 (Sigma). After 30 min of saturation, the sections are incubated in the presence of a mouse monoclonal antibody specific to nestin (abcam), a rabbit polyclonal antibody specific to OCT4 or SOX2 (Abcam), and then an anti-mouse secondary antibody coupled to a fluorochrome (Invitrogen)

or anti-rabbit coupled to a fluorochrome (Invitrogen). The sections of SKP-like cells are then examined with the epifluorescence microscope (Nikon Eclipse 80i microscope).

Results:

The microscopy observations (magnification *40) showed an increase in intensity of SOX2, OCT4 and nestin labeling in the conditions in which the synergistic extract obtained according to example 1 was applied, compared to the untreated. FIG. 7 reproduces the photographs obtained for the SOX2 and nestin labeling.

Conclusions:

Application of 1% of the synergistic extract obtained according to example 1 in SKP-like cells stimulates expression of the SOX2, OCT4 and nestin stem cell markers.

The invention claimed is:

1. A method of obtaining an extract of *Palmaria palmata* alga and of flower heads of a plant of the genus *Jasminum* that comprises:
   a) dissolving an amount of dried and finely ground *Palmaria palmata* alga in water in a weight ratio of water to *Palmaria palmata* between 10/1 and 50/1;
   b) hydrolyzing the aqueous solution of *Palmaria palmata* alga with a carbohydrase and/or an endoprotease at a pH between 3 and 6, at a temperature between 40° C. and 80° C., for a time of at least 1 hour;
   c) after optional addition of a filter aid and centrifugation, obtaining an aqueous extract of *Palmaria palmata* alga;
   d) macerating dried flower heads of a plant of the genus *Jasminum* for a time of at least 2 hours and at most 4 hours at ambient temperature in the aqueous extract of *Palmaria palmata* alga obtained in c); the weight ratio of the dry weight of the alga to the dry weight of the flower heads being between 40/60 and 95/5;
   e) filtering the macerated product that is obtained at the end of d) to recover an extract of *Palmaria palmata* alga and of flower heads of a plant of the genus *Jasminum*, which is heated for at least 2 hours and for up to 24 hours, at a temperature between 40° C. and 90° C., to deactivate the carbohydrase and endoprotease enzymes; and
   f) purifying the product that is obtained at the end of e) to obtain the extract of *Palmaria palmata* alga and of flower heads of a plant of the genus *Jasminum*.

2. The method of claim 1, in which the aqueous solution of *Palmaria palmata* alga is hydrolyzed at a pH between 4 and 5.5.

3. The method of claim 2, wherein the pH is between 4 and 4.5.

4. The method of claim 1, in which the aqueous solution of *Palmaria palmata* alga is hydrolyzed at a temperature between 50° C. and 60° C.

5. The method of claim 4, wherein the aqueous solution of *Palmaria palmata* alga is hydrolyzed at a temperature between 50° C. and 55° C.

6. The method of claim 1, in which the aqueous solution of *Palmaria palmata* alga is hydrolyzed for a time of 2 hours.

7. The method of claim 1, in which the product that is obtained at the end of d) is purified by filtration.

8. The method of claim 1, in which the weight ratio of water to *Palmaria palmata* alga is between 20/1 and 40/1.

* * * * *